US012747220B2

(12) United States Patent
Kumar V et al.

(10) Patent No.: US 12,747,220 B2
(45) Date of Patent: Sep. 29, 2026

(54) METHOD FOR PREPARATION OF 1-(2-((2,4-DIMETHYLPHENYL)THIO)PHENYL) PIPERAZINE AND ITS SALTS

(71) Applicant: R L FINE CHEM PRIVATE LIMITED, Bangalore (IN)

(72) Inventors: Vinay Kumar V, Bangalore (IN); Dantham Sowmya, Bangalore (IN); Rajat Rudragoud Biradar Patil, Bangalore (IN); Puttaraju Boregowda, Bangalore (IN); Sivakumar Rallapalli, Bangalore (IN)

(73) Assignee: R L FINECHEM PRIVATE LIMITED, Bangalore (IN)

( * ) Notice: Subject to any disclaimer, the term of this patent is extended or adjusted under 35 U.S.C. 154(b) by 496 days.

(21) Appl. No.: 18/272,875

(22) PCT Filed: Jul. 16, 2021

(86) PCT No.: PCT/IB2021/056441

§ 371 (c)(1),
(2) Date: Jul. 18, 2023

(87) PCT Pub. No.: WO2022/254248

PCT Pub. Date: Dec. 8, 2022

(65) Prior Publication Data

US 2024/0101524 A1 Mar. 28, 2024

(30) Foreign Application Priority Data

May 31, 2021 (IN) ............................ 202141024116

(51) Int. Cl.

| | |
|---|---|
| ***C07D 295/096*** | (2006.01) |
| ***B01J 27/122*** | (2006.01) |
| ***C07C 319/06*** | (2006.01) |
| ***C07C 319/18*** | (2006.01) |
| ***C07C 319/20*** | (2006.01) |
| ***C07C 323/47*** | (2006.01) |

(52) U.S. Cl.

CPC ........ *C07D 295/096* (2013.01); *B01J 27/122* (2013.01); *C07C 319/06* (2013.01); *C07C 319/18* (2013.01); *C07C 319/20* (2013.01); *C07C 323/47* (2013.01)

(58) Field of Classification Search

None

See application file for complete search history.

(56) References Cited

U.S. PATENT DOCUMENTS 9,493,409 B2 11/2016 Zupancic

FOREIGN PATENT DOCUMENTS

| | | | |
|---|---|---|---|
| WO | 2003/029232 | A1 | 4/2003 |
| WO | 2007/144005 | A1 | 12/2007 |
| WO | 2014/191548 | A1 | 12/2014 |
| WO | 2017/029377 | A1 | 2/2017 |

OTHER PUBLICATIONS

Oct. 8, 2021 International Search Report issued in International Patent Application No. PCT/IB2021/056441.

Oct. 8, 2021 Written Opinion issued in International Patent Application No. PCT/IB2021/056441.

*Primary Examiner* — Samantha L Shterengarts

(74) *Attorney, Agent, or Firm* — Oliff PLC

(57) ABSTRACT

A method for preparation of 1-(2-((2,4-Dimethylphenyl) thio)phenyl)piperazine and its salts through a novel intermediate, 2-((2,4-dimethylphenyl)thio)-N-hydroxybenzamide involves mild conditions, eco-friendly and cost effective reagents to provide the target compound with purity level greater than 99.5% in high yield.

15 Claims, 7 Drawing Sheets

(a)

(b)

(a)

(b)

METHOD FOR PREPARATION OF 1-(2-((2,4-DIMETHYLPHENYL)THIO)PHENYL) PIPERAZINE AND ITS SALTS

TECHNICAL FIELD

The present invention is in relation to synthetic organic chemistry. In particular to a method of preparation of 1-(2-((2,4-Dimethylphenyl)thio)phenyl)piperazine and its salts.

The method involves mild conditions, eco-friendly and cost effective reagents and to beget the compound in high yield in few steps.

BACKGROUND AND PRIOR ART

Depression is a mood disorder that can affect a person's daily life. It is commonly described as feelings of sadness, loss, or anger. The causes of depression are many including genetics, age, illness, abuse and the like.

Depression is treated and the symptoms are managed usually involving good support, psychotherapy and drug treatment. Drugs commonly known as antidepressants can help treat moderate-to-severe depression. The class of antidepressants include but not limiting to selective serotonin reuptake inhibitors (SSRIs), monoamine oxidase inhibitors (MAOIs), tricyclic antidepressants, selective serotonin and norepinephrine reuptake inhibitors (SNRIs).

1-(2-((2,4-Dimethylphenyl)thio)phenyl)piperazine contributes as serotonin modulator and stimulator (SMS) in the management of depression. It inhibits the reuptake of serotonin and act as a serotonin receptor agonist (5-HT1A). The 1-(2-((2,4-Dimethylphenyl)thio)phenyl)piperazine and its salts are is in great demand owing to its potential as antidepressant and the increasing population with depression.

There are documents which disclose the synthesis of 1-(2-((2,4-Dimethylphenyl)thio)phenyl)piperazine and its salts. WO2007144005 discloses a method which require the use of expensive starting materials, toxic palladium catalyst and phosphine ligand. WO2003029232 discloses a method that is not suitable for large scale production as it is low yielding and unsuitable for large scale production of 1-(2-((2,4-Dimethylphenyl)thio)phenyl)piperazine. In another document WO/2017/029377, preparation of 1-(2-((2,4-Dimethylphenyl)thio)phenyl)piperazine hydrobromide is described. The reaction is cumbersome and involves expensive coupling reagents and protecting groups.

There is a consistent demand for developing the compound in an environmentally benign and economically way for the benefit of the society. The present invention aims to develop a simple high yielding process to fill the lacuna of the prior art methods.

SUMMARY OF INVENTION

Accordingly the present invention provides a facile, economical method adoptable for large scale preparation of 1-(2-((2,4-Dimethylphenyl)thio)phenyl)piperazine and its salts.

The invention provides a method for preparation of 1-(2-((2,4-Dimethylphenyl)thio)phenyl)piperazine and its salts comprising acts of—preparing 2-Mercaptobenzoic acid (2) from 2,2'-disulfanediyldibenzoic acid (1) in a solvent in presence of base and metal catalyst, coupling 2-Mercaptobenzoic acid (2) with 1-Bromo-2,4-dimethylbenzene (4) to obtain 2-((2,4-dimethylphenyl)thio)benzoic acid (5) in presence of metal catalyst, reacting 2-((2,4-dimethylphenyl)thio)benzoic acid (5) with halogenating agent and hydroxyl amine hydrochloride to obtain 2-((2,4-dimethylphenyl)thio)-N-hydroxybenzamide (6), heating 2-((2,4-dimethylphenyl)thio)-N-hydroxybenzamide (6) in presence of base to obtain 2-((2,4-dimethylphenyl)thio)aniline and converting to 2-((2,4-dimethylphenyl)thio) aniline hydrochloride (7), reacting 2-((2,4-dimethylphenyl)thio)aniline hydrochloride (7) with Bis(2-chloroethyl)amine hydrochloride (8) to obtain 1-(2-((2,4-Dimethylphenyl)thio)phenyl) piperazine hydrochloride (9), and converting 1-(2-((2,4-Dimethylphenyl)thio)phenyl)piperazine hydrochloride (9) optionally to 1-(2-((2,4-Dimethylphenyl)thio)phenyl)piperazine or its salt.

The invention also provides a stable intermediate compound of formula (6) for the synthesis of 1-(2-((2,4-Dimethylphenyl)thio)phenyl)piperazine or its salts Formula (6)

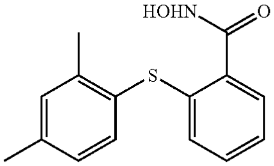

The invention also provides a method of preparation of 1-(2-((2,4-Dimethylphenyl)thio)phenyl)piperazine and its salts starting from intermediate (6), said method comprising acts of— heating 2-((2,4-dimethylphenyl)thio)-N-hydroxybenzamide (6) in presence of base in a solvent to obtain 2-((2,4-dimethylphenyl)thio)aniline and converting to 2-((2,4-dimethylphenyl)thio)aniline hydrochloride (7), reacting 2-((2,4-dimethylphenyl)thio)aniline hydrochloride (7) with Bis(2-chloroethyl)amine hydrochloride (8) in a solvent to obtain 1-(2-((2,4-Dimethylphenyl) thio)phenyl)piperazine hydrochloride (9), and converting 1-(2-((2,4-Dimethylphenyl)thio)phenyl)piperazine hydrochloride (9) optionally to 1-(2-((2,4-Dimethylphenyl)thio)phenyl)piperazine or its salt.

The present invention provides a method for preparation of various salts of 1-(2-((2,4-Dimethylphenyl)thio)phenyl) piperazine including hydrochloride, hydrobromide and fumarate salts.

BRIEF DESCRIPTION OF FIGURES

The present invention will be readily understood by the following description in conjunction with the accompanying figures in which.

DETAILED DESCRIPTION OF INVENTION

Figure 1:
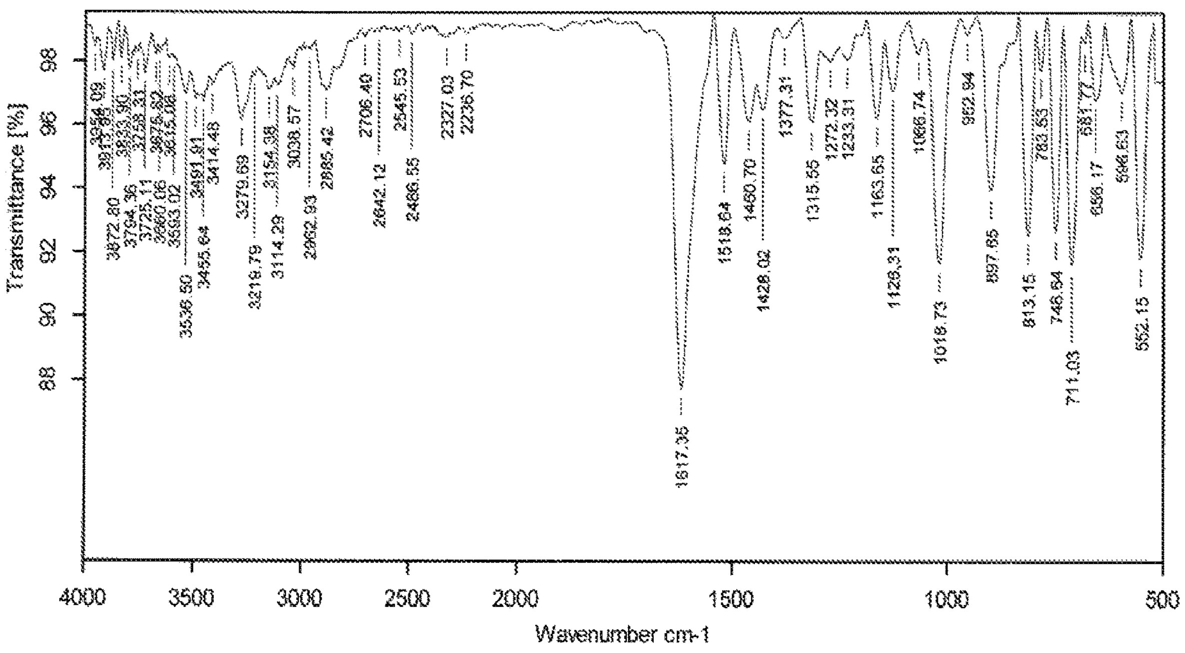
FIG. 1: shows IR spectrum of 2-((2,4-dimethylphenyl) thio)-N-hydroxybenzamide (6).

The foregoing description of the embodiments of the invention has been presented for the purpose of illustration. It should not be construed that the scope of the invention is limited to the disclosure herein.

The various embodiments of the method of preparation of are described below with reference to the figures.

It may further be noted that as used herein and in the appended claims, the singular forms "a", "an", and "the" include plural reference unless the context clearly dictates otherwise. Unless defined otherwise, all technical and scientific terms used herein have the same meanings as commonly understood by person skilled in the art.

The present invention provides a high yielding method for synthesis of 1-(2-((2,4-Dimethylphenyl)thio)phenyl)piperazine. HBr of formula 11 and other salts viable on large scale economically.

Synthetic Procedure for Formula 11 is Given in Scheme-I Below

Scheme-1

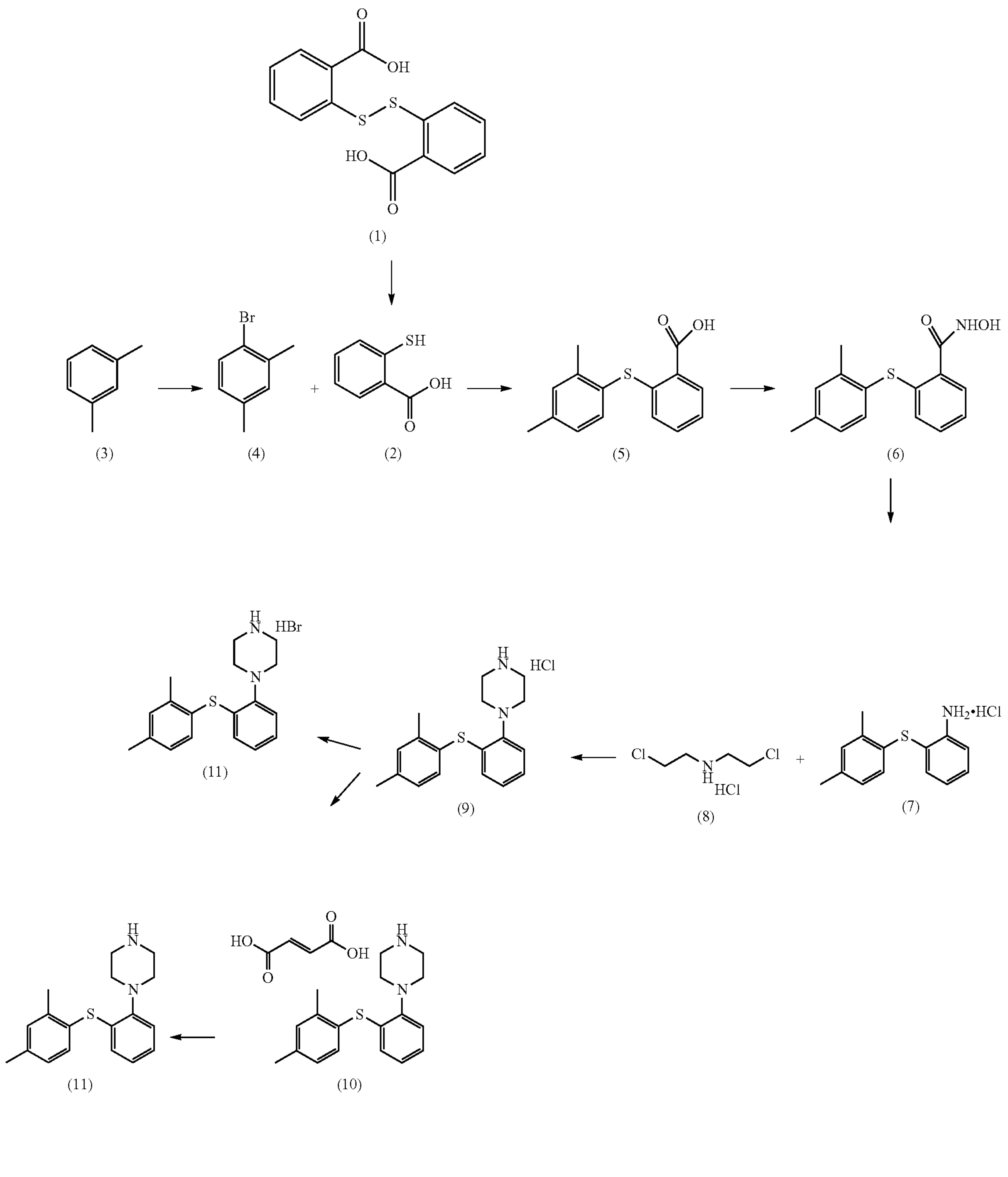

In an embodiment the present invention demonstrates a method of preparation of 1-(2-((2,4-Dimethylphenyl)thio)phenyl)piperazine and its salts through novel intermediate 2-((2,4-dimethylphenyl)thio)-N-hydroxybenzamide (6), in three stages. The salts may be selected from a group comprising hydrochloride salt (9), fumarate salt (10) and hydrobromide salt (11).

Stage I: Preparation of Intermediate 2-((2,4-dimethylphenyl)thio)-N-hydroxybenzamide (6)

In an embodiment the novel intermediate 2-((2,4-dimethylphenyl)thio)-N-hydroxybenzamide (6) is prepared through three steps.

In step I, 2-mercaptobenzoic acid (2) is prepared from the 2,2'-disulfanediyldibenzoic acid (1) with Zinc and base.

(1)

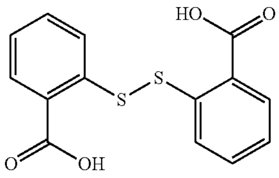

(2)

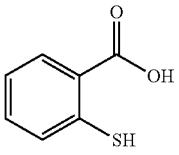

In step II, 2-mercaptobenzoic acid (2) is coupled with 1-bromo-2,4-dimethylbenzene (4) in the presence of Cu powder to obtain 2-((2,4-dimethylphenyl)thio)benzoic acid (5).

(4)

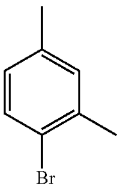

(5)

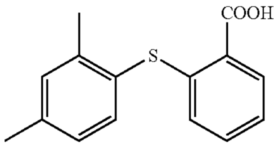

In step III, the 2-((2,4-dimethylphenyl)thio)benzoic acid (5) is treated with thionyl chloride and hydroxyl amine hydrochloride to beget novel intermediate 2-((2,4-dimethylphenyl)thio)-N-hydroxybenzamide (6).

(6)

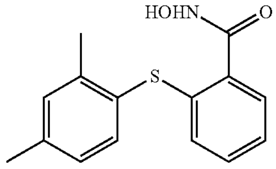

Figure 3:
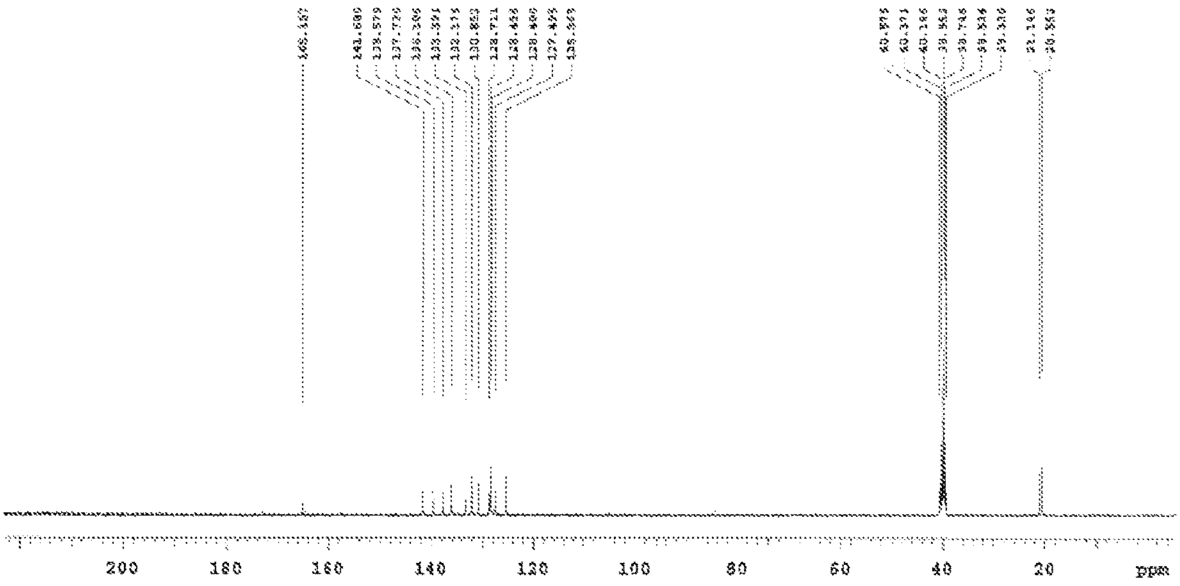
FIG. 3: shows $^{13}$CNMR spectrum of 2-((2,4-dimethylphenyl)thio)-N-hydroxybenzamide (6).
Figure 4:
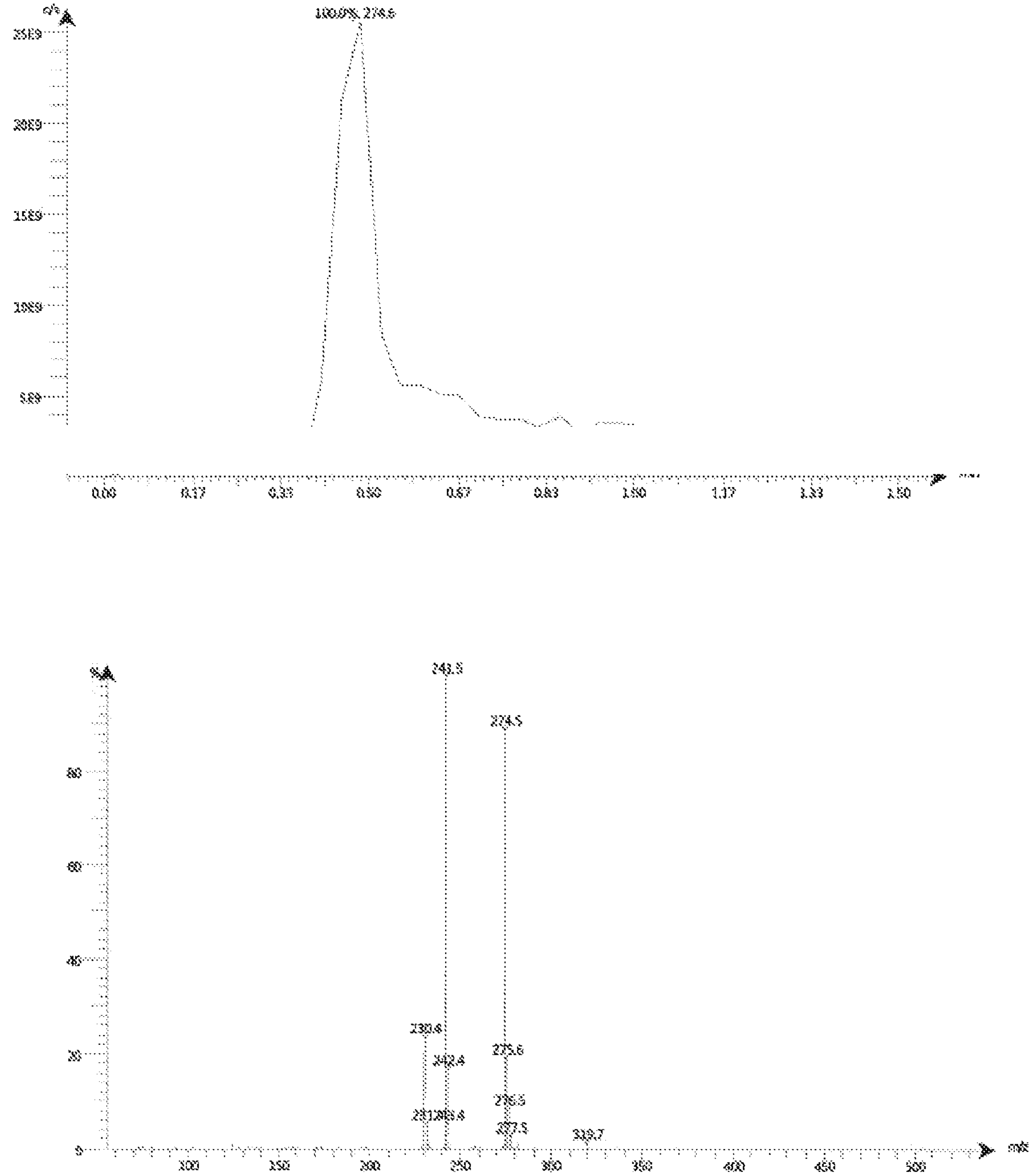
FIG. 4: shows Mass spectrum of 2-((2,4-dimethylphenyl) thio)-N-hydroxybenzamide (6).

In an embodiment, the 2-((2,4-dimethylphenyl)thio)-N-hydroxybenzamide (6) is characterised by IR (FIG. 1), $^{1}$HNMR (FIG. 2), $^{13}$NMR (FIG. 3), and mass spectral analysis (FIG. 4).

IR (Neat): 1018, 1315, 1518, 1617, 3279 $cm^{-1}$ (FIG. 1)

Figure 2:
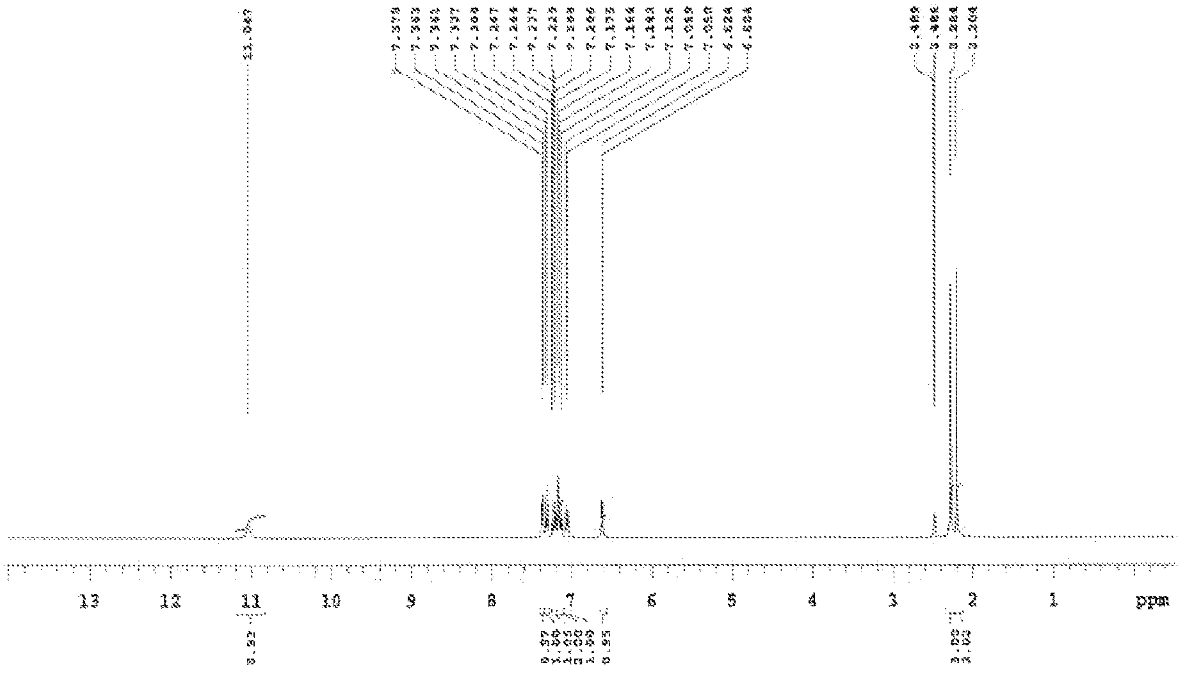
FIG. 2: shows $^{1}$HNMR spectrum of 2-((2,4-dimethylphenyl)thio)-N-hydroxybenzamide (6).

$^{1}$HNMR (DMSO-$d_6$, 400 MHz): δ 11.04 (br, s, 1H), 7.37 (m, 1H), 7.31 (d, J=7.6 Hz, 1H), 7.24 (m, '1H), 7.17-7.12 (m, 2H), 7.06 (d, J=7.6 Hz, 1H), 6.62 (d, J=8.0 Hz, 1H), 2.28 (s, 3H), 2.20 (s, 3H). (FIG. 2)

$^{13}$NMR (DMSO-$d_6$, 100 MHz): δ 165.15, 141.68, 139.57, 137.73, 136.10, 133.39, 132.17, 130.85, 128.71, 128.45, 128.40, 127.49, 125.36, 21.14, 20.55. (FIG. 3)

Mass APCI of $C_{15}H_{15}NO_2S$: 274.5 (M+1). (FIG. 4)

Figure 5:
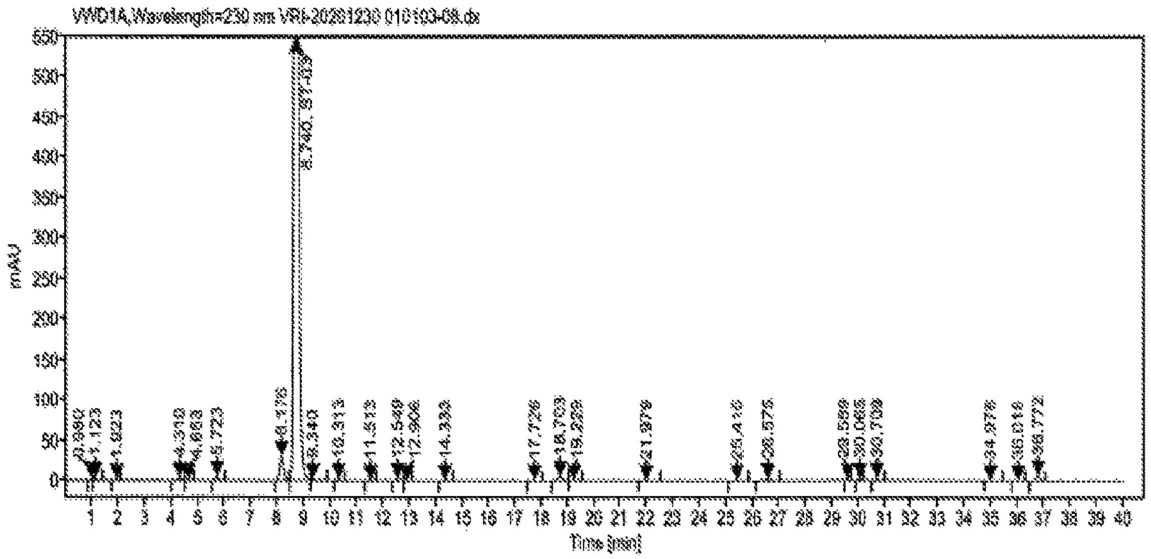
FIG. 5: shows a) HPLC chromatogram of 2-((2,4-dimethylphenyl)thio)-N-hydroxybenzamide (6) after its immediate preparation and (b) taken after six months; indicating the stability for over six months.
Figure 5:
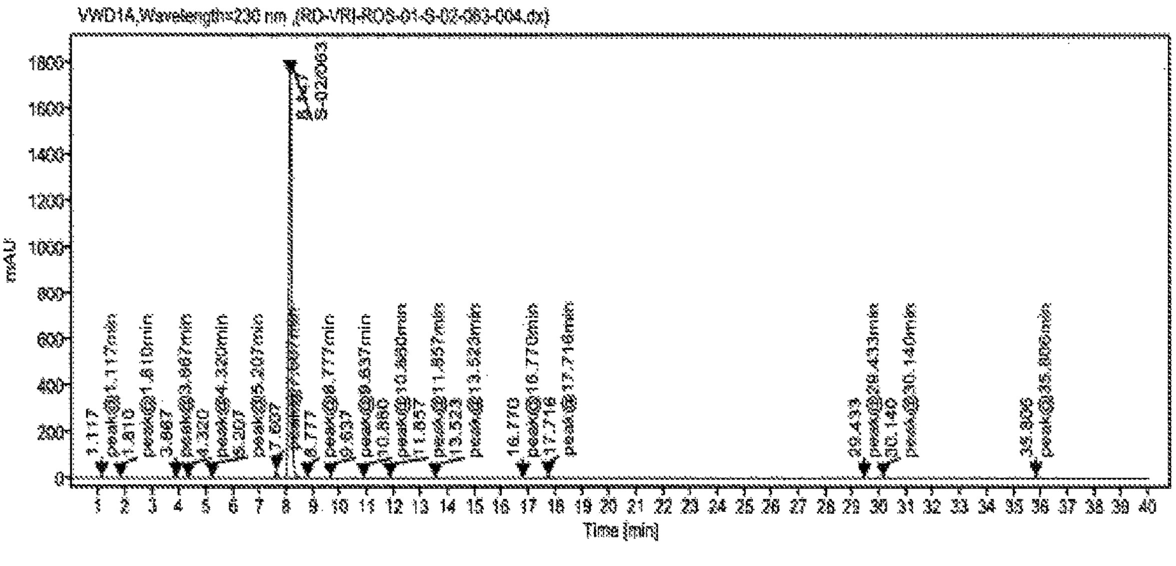
Figure 6:
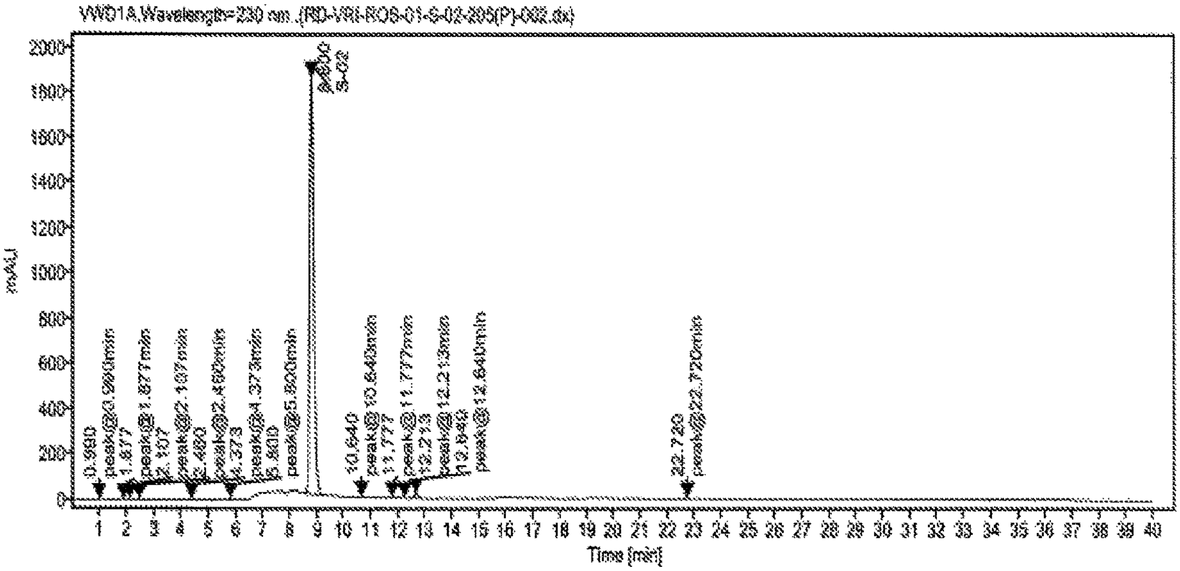
FIG. 6: shows HPLC chromatogram of purified 2-((2,4-dimethylphenyl)thio)-N-hydroxybenzamide (6) which indicates purity of 97.86%.
Figure 7:
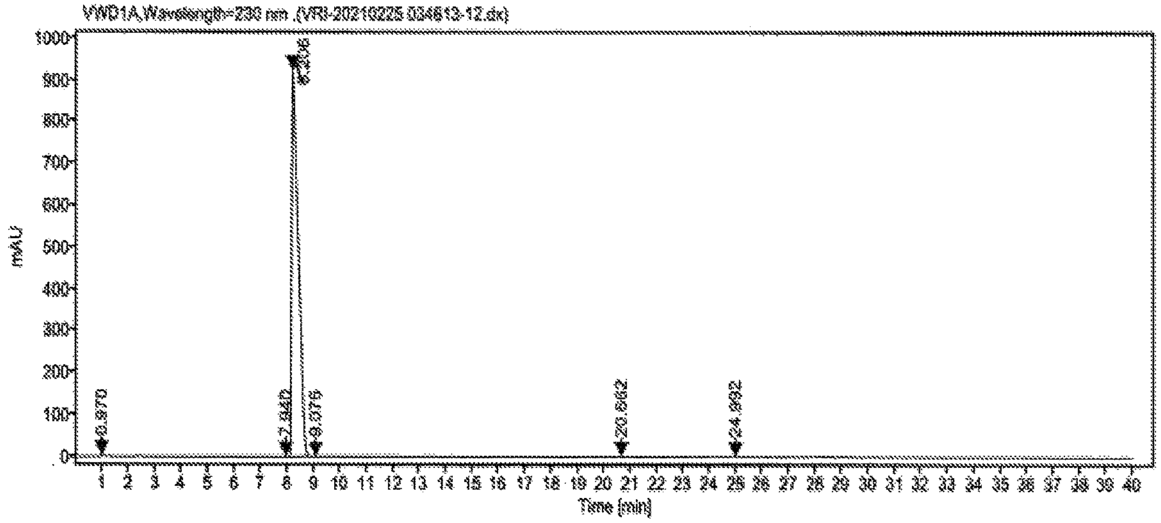
FIG. 7: shows HPLC chromatograms of 1-(2-((2,4-Dimethylphenyl)thio)phenyl)piperazine hydrobromide (11) (a) indicating purity of about 99.77% and (b) indicating purity of about 99.68%.
Figure 7:
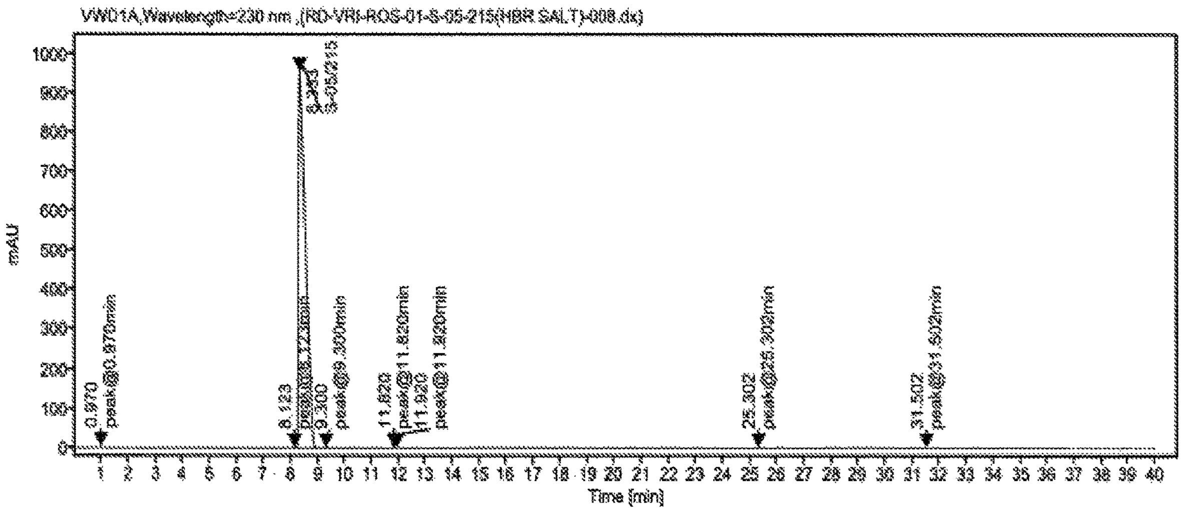

In another embodiment, the purity of the intermediate (6) is analysed by HPLC analysis (95.5% to 97.8%) FIG. 6. Intermediate (6) is found to be a stable compound as noted by re-analysis of spectral purity from the HPLC data, the sample demonstrated negligible variation after six months from HPLC data—FIG. 5*a* (initial sample) and FIG. 5*b* (sample analysed after six months).

Stage II: Preparation of 1-(2-((2,4-dimethylphenyl) thio)phenyl) aniline hydrochloride (7)

In another embodiment the intermediate 2-((2,4-dimethylphenyl)thio)-N-hydroxybenzamide (6) undergoes rearrangement on heating in different organic solvents like DMSO and dimethyl carbonate to amine and is isolated as a Hydrochloride salt viz. 2-((2,4-dimethylphenyl)thio)aniline hydrochloride (7) by treating with IPA.HCl.

(7)|

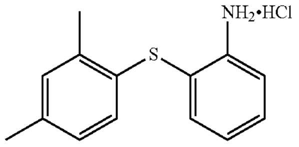

Stage III Preparation of 1-(2-((2,4-dimethylphenyl)thio)phenyl)piperazine or its Salts In still another embodiment 2-((2,4-dimethylphenyl)thio) aniline hydrochloride (7) is treated with Bis(2-chloroethyl) amine hydrochloride (8) to produce 1-(2-((2,4-dimethylphenyl)thio)phenyl) piperazine hydrochloride (9), which is further converted into 1-(2-((2,4-dimethylphenyl)thio)phenyl)piperazine (free base) or its salts of fumaric acid (10) and hydrobromide (11). Figure (7a) and (7b) indicates the purity of the hydrobromide salt is above 99.6%.

(8)

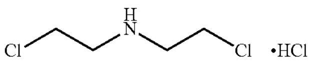

-continued (9)

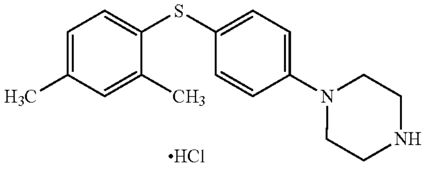

(11)

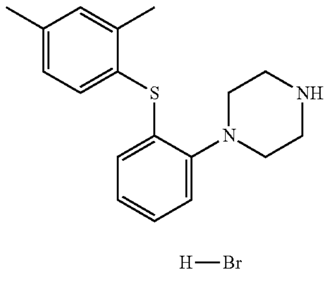

In an embodiment the base may be selected from a group comprising Sodium hydroxide, Potassium hydroxide, Sodium methoxide, Sodium carbonate, Potassium carbonate, Sodium bicarbonate, Triethylamine, Triazabicyclodecene, 1,8-Diazabicyclo[5.4.0]undec-7-ene, and 1,5-Diazabicyclo[4.3.0]non-5-ene.

In another embodiment the solvent is selected from a group comprising solvents of Toluene, ethylene dichloride, 1,4-Dioxane, Diglyme, Monoethylene Glycol, Sulfolane, Chlorobenzene, Dichlorobenzene, m-Xylene, Methanol, n-Butanol, Isopropyl acetate, Isobutanol, Dimethyl sulphoxide, N-Methyl-2-Pyrrolidone and Dimethylacetamide.

In another embodiment, the metal catalysts are selected from zinc and copper.

In another embodiment, the phase transfer agent is selected from Polyethylene glycol (PEG), Tetrabutyl Ammonium Bromide (TBAB).

In still another embodiment the chlorinating reagents are NaOCl, $PCl_3$, $PCl_5$ and $SOCl_2$.

In still another embodiment the brominating agent is selected from a group comprising Potassium bromide, Sodium bromide, Hydrogen bromide, and Bromine.

EXPERIMENTAL

A. Preparation of 2-mercaptobenzoic acid (2)

Example 1

A solution of 500 mL (2M, NaOH solution) is charged in to clean 1 L flask, 2,2'-disulfanediyldibenzoic acid (1) (100 g, 326 mmol) is added and temperature raised to 45-50° C. to get homogenous solution. Zn (63 g, 974 mmol) powder is added in to reaction mixture, after addition the reaction is maintained at 45-50° C. for 30 min, and the reaction temperature is raised to 90-95° C. and maintained for 10-12 h. After completion, reaction mixture is allowed to cool for 20° C.-35° C. and filtered to remove Zn powder, aqueous layer is acidified with 6N HCl to get 2-mercaptobenzoic acid as a white solid. The isolated weight is 90 g (90% yield) with HPLC purity 95%.

B. Preparation of 1-bromo-2,4-dimethylbenzene (4)

Example 2

To the reaction flask m-Xylene (3)(1 Kg, 9.4 mmol) is added and cooled to about 0-10° C., followed by the addition of Iron powder (1%, w/w) in to reaction mixture. Liquid bromine (1.6 Kg, 10 mmol) is added to reaction mixture over a period of 2-3 h and the completion of the reaction is monitored by GC analysis. Then the reaction mixture is quenched with NaOH solution (1.5 Kg dissolve in 3000 L water) and filtered through celite bed, to remove iron powder. The resulting mixture is allowed to separate, organic layer is separated and dried using sodium sulphate to get required 1-bromo-2,4-dimethylbenzene as yellow liquid. The isolated weight is 1.5 Kg (90% yield) with HPLC purity 85% along with 10% of m-xylene.

Example 3

To the reaction flask, m-Xylene (3)(100 g, 943 mmol) is added and the temperature is raised to 40-45° C., followed by the addition of Iron powder (1%, w/w) in to reaction mixture. Liq Bromine (164 g, 1037 mmol) is added to reaction mixture over a period of 1-2 h and completion of the reaction is monitored by GC analysis. The reaction mixture is quenched using NaOH solution (150 g dissolve in 300 mL water) and filtered through celite bed, to remove iron powder. The resulting mixture is allowed to separate, the organic layer is separated and dried by sodium sulphate to get required 1-bromo-2,4-dimethylbenzene as yellow liquid. The isolated weight is 145 Kg (84% yield) with HPLC purity 80% along with 10% of m-xylene.

Example 4

To the reaction flask m-Xylene (3) (10 g, 94 mmol) is added followed by the addition of pyridine (0.3 eq) and $HNO_3$ (0.3 eq) in to reaction mixture. aq HBr (16.6 g, 103 mmol) is added to reaction mixture over a period of 20-30 min and maintained at 55-60° C. for 6-7 h, the completion of the reaction is monitor by GC analysis. Then the reaction mixture is quenched using NaOH solution (15 g dissolve in 30 mL water) and the reaction mixture is filtered through celite bed, to remove iron powder. Then the resulting mixture is allowed to separate, the organic layer is separated and dried by sodium sulphate to get required 1-bromo-2,4-dimethylbenzene as yellow liquid. The isolated weight is 12 g (70% yield) with HPLC purity 94% along with 4.5% of m-xylene.

Example 5

To the reaction flask NaBr (14.5 g, 141 mmol) was added, 10 mL of water (0.3 eq) was charged, dropwise addition of HCl (18 mL) was added followed by the addition of m-xylene (10 g 94 mmol) then dropwise addition of NaOCl (1.5 eq, 10% solution in water) to reaction mixture over a period of 20-30 min, the reaction was maintained at 30-35° C. for 4-5 h, completion of the reaction was monitored by GC analysis. Organic layer was separated and extracted with MDC dried over anhydrous sodium sulphate to get 1-bromo-2,4-dimethylbenzene as yellow liquid. The isolated weight 7 g (41% yield) with HPLC purity 79% along with 19% of m-xylene.

C: Preparation of 2-((2,4-dimethylphenyl)thio)benzoic acid (5)

Example: 6

A mixture of DMSO/DMA (1:1) is charged in to 1 L flask, 100 g (649 mmol) of 2-mercaptobenzoic acid (2) is added under nitrogen atmosphere, followed by the addition of 1-bromo-2,4-dimethylbenzene (4) (142 g, 779 mmol) to the reaction mixture, and the reaction temperature is raised to 45-50° C. $K_2CO_3$ (134 g, 940 mmol) is added to reaction mixture at about 45-50° C. followed by the addition of Cu (2 g, 2% w/w), CuI (2 g, 2% w/w) and TBAB (5 g, 5% w/w) and the reaction mixture is stirred at about 140-145° C. for 8-10 h to give 2-((2,4-dimethylphenyl)thio)benzoic acid. After completion, the reaction mixture is quenched with water and maintained under stirring for 30 min at 40° C. Then the reaction mixture is filtered through celite bed to remove Cu catalyst, and the filtrate is acidified with 6N HCl to give off white to light brown crude solid. The crude solid is suspended with IPA (2 v) and maintained at 60° C. for 1-2 h and cool to 20° C.-35° C. and the solid mass is filtered to obtain off white solid. The isolated weight is 110 g (65% yield) with HPLC purity 93%.

Example 7

A mixture of DMSO (3 v, 150 mL) and 100 g (649 mmol) of 2-mercaptobenzoic acid (2) is charged under nitrogen atmosphere, followed by the addition of 1-bromo-2,4-dimethylbenzene (4) (142 g, 779 mmol) to the reaction mixture, and the reaction mixture temperature is raised to 45-50° C. $K_2CO_3$ (134 g, 940 mmol) is added to reaction mixture at 45-50° C. followed by the addition of Cu (2 g, 2% w/w), CuI (2 g, 2% w/w) and TBAB (5 g, 5% w/w) and the reaction mixture is stirred at 140° C. for 16 h to give 2-((2,4-dimethylphenyl)thio)benzoic acid. After completion, the reaction mixture is quenched with 4 v of water and maintained under stirring for 30 min at 40° C. Then the reaction mixture is filtered through celite bed to remove Cu catalyst, and the filtrate is acidified with 6N HCl to give off white to light brown crude solid. The crude solid is suspended with acetone (2 v) and maintained at 50° C. for 1-2 h, cooled to 20° C.-35° C. and filtered the solid mass to obtain yellow solid. The isolated weight is 140 g (83% yield) with HPLC purity 94%.

Example 8

DMSO (3 v 150 mL) is charged in to 1 L flask, and 100 g (649 mmol) of 2-mercaptobenzoic acid (2) is added under nitrogen atmosphere, followed by the addition of 1-bromo-2,4-dimethylbenzene (4) (142 g, 779 mmol). The reaction temperature is raised to 45-50° C. $K_2CO_3$ (134 g, 940 mmol) to reaction mixture at 45-50° C. followed by the addition of Cu (1 g, 1% w/w), CuI (1 g, 1% w/w) and PEG-400 (5 g, 5% w/w) and the reaction mixture is stirred at 140° C. for 16 h to give 2-((2,4-dimethylphenyl)thio)benzoic acid. After completion, the reaction mixture is quenched with 4 v of water and maintained under stirring for 30 min at 40° C. Then the reaction mixture is filtered through celite bed to remove Cu catalyst, and the filtrate is acidified with 6N HCl to give off white to light brown crude solid. The crude solid is suspended with acetone (2 v) and maintained at 50° C. for 1-2 h, cooled to 20° C.-35° C. and filtered the solid mass to obtain yellow solid. The isolated weight is 145 g (86% yield) with HPLC purity 74%.

Example 9

A mixture of DMSO/DMA (1:1.15 mL/15 mL) is charged in to 250 mL flask. 10 g (64.9 mmol) of 2-mercaptobenzoic acid (2) is added under nitrogen atmosphere, followed by 1-bromo-2,4-dimethylbenzene (4) (14.2 g, 77.9 mmol), the reaction mixture temperature is raised to 45-50° C. Then $K_2CO_3$ (13.4 g, 94.0 mmol) is added to reaction mixture at 45-50° C. followed by the addition of Cu (2% w/w), CuI (2% w/w) and the reaction mixture is stirred at 140-145° C. for 8-10 h to give 2-((2,4-dimethylphenyl)thio)benzoic acid. After completion, the reaction mixture is quenched with 4 v of water and maintained under stirring for 30 min at 40° C. Then the reaction mixture is filtered through celite bed to remove Cu catalyst, and the filtrate is acidified with 6N HCl to give off white to light brown crude solid. The crude solid is suspended in IPA and maintained at 60° C. for 1-2 h, cooled to 20° C.-35° C. and filter the solid mass to obtain off white solid. The isolated weight is 11 g (65% yield) with HPLC purity 90%.

Example 10

A mixture of DMSO/DMA (1:1.15 mL/15 mL) is charged in to 250 mL flask, 10 g (64.9 mmol) of 2-mercaptobenzoic acid (2) is added under nitrogen atmosphere, followed by the addition of 1-bromo-2,4-dimethylbenzene (4) (14.2 g, 77.9 mmol). The reaction mixture temperature is raised to 45-50° C. $K_2CO_3$ (13.4 g, 94.0 mmol) to reaction mixture at 45-50° C. followed by the addition of Cu (1% w/w), CuI (1% w/w) and the reaction mixture is stirred at 140-145° C. for 18-20 h to give 2-((2,4-dimethylphenyl)thio)benzoic acid. After completion, the reaction mixture is quenched with water and maintained under stirring for 30 min at 40° C. The reaction mixture is filtered through Celite bed to remove Cu catalyst, and the filtrate is acidified with 6N HCl to give off white to light brown crude solid. The crude solid is suspended in IPA and maintained at 60° C. for 1-2 h, cooled to 20° C.-35° C. and filtered the solid mass to obtain off white solid. The isolated weight is 11 g (65% yield) with HPLC purity 93%.

D: Preparation of 2-((2,4-dimethylphenyl)thio)-N-hydroxybenzamide (6)

Example 11

A mixture of 100 g (387 mmol) of 2-((2,4-dimethylphenyl)thio)benzoic acid (5) in 300 mL of EDC is charged into a flask. The temperature of reaction mixture is raised to 45-50° C. Thionyl chloride (91 g, 775 mmol) is added drop wise in to reaction mixture over a period of 30 min, followed by the addition of catalytic amount of DMF and maintained at 75-80° C. under stirring for 7-8 h. After completion of the reaction, the excess thionyl chloride is distilled out under vacuum. Then the reaction mixture is quenched with $NH_2OH\cdot HCl$ solution (Dissolve $NH_2OH$. HCl, 40 g, 580 mmol & $NaHCO_3$, 65 g, 775 mmol) and stirred at 30-35° C. for 7-8 h. After completion, the reaction mass is filtered and washed with EDC to obtain 2-((2,4-dimethylphenyl)thio)-N-hydroxybenzamide as off white solid. The isolated weight is 78 g (75% yield) with HPLC purity 97%.

E: Preparation of 2-((2,4-dimethylphenyl)thio)aniline hydrochloride (7)

Example 12

A mixture of 100 g (336 mmol) of 2-((2,4-dimethylphenyl)thio)-N-hydroxybenzamide (6) and methanol (3.5 g, 109 mmol) are charged in dimethyl carbonate (1,5 v, 150 mL), followed by addition of $Et_3N$ (11 g, 109 mmol), the reaction mixture is stirred at 70° C. for 8-9 h. After completion of the reaction, excess dimethyl carbonate is distilled out under vacuum, diluted with water and extracted with MTBE. The organic layer is separated and IPA. HCl (0.5 v) is added dropwise to the organic layer over a period of 15 min to get 2-((2,4-dimethylphenyl)thio)aniline hydrochloride as white solid. The isolated weight is 60 g (60% yield) with HPLC purity 97%.

Example 13

A mixture of 10 g (33.6 mmol) of 2-((2,4-dimethylphenyl) thio)-N-hydroxybenzamide (6) and DMSO (5 v, 50 mL) are charged in to 250 mL RBF, followed by the addition of K2$CO_3$ (7.4 g, 54.9 mmol). The reaction mixture is stirred at 70° C. for 16-18 h. After completion, the reaction mixture is diluted with 6 v of water and extracted by MTBE. The organic layer is separated and IPA. HCl is added dropwise to the organic layer over a period of 15 min to get 2-((2,4-dimethylphenyl)thio)aniline hydrochloride as white solid. The isolated weight is 38 g (40% yield) with HPLC purity 98%.

F. Preparation of 1-(2-((2,4-dimethylphenyl)thio) phenyl)piperazine hydrochloride (9)

Example 14

A mixture of 100 g (436 mmol) of 2-((2,4-dimethylphenyl)thio)aniline (7) and bis(2-chloroethyl)amine hydrochloride (8) (85 g, 480 mmol) are charged into 1,2-dichlorobenzene (4 v, 400 mL) and maintained at 160-170° C. for 12-15 h. After completion, the reaction mixture is cooled to 20° C.-35° C., diluted with toluene (4 v) and maintained for 1-2 h under stirring. The solid mass is filtered and washed with 1 v of toluene to get 1-(2-((2,4-dimethylphenyl)thio)phenyl) piperazine hydrochloride (9) white solid. The isolated weight 89 g (61% yield) with HPLC purity 98.4%.

Example 15

A mixture of 100 g (436 mmol) of 2-((2,4-dimethylphenyl)thio)aniline (7) and bis(2-chloroethyl)amine hydrochloride (8) (85 g, 480 mmol) are charged into Methyl digol (4 v, 400 mL), the reaction mixture is maintained at 150-155° C. for 12-15 h. After completion, the reaction mixture is cooled to 20° C.-35° C., and the solid obtained is diluted with toluene (3 v) and water (4 v) and maintain for 2 h under stirring. The solid mass is filtered and washed with 1 v of toluene to get 1-(2-((2,4-dimethylphenyl)thio)phenyl)piperazine hydrochloride (9) as off white to white solid. The isolated weight is 73 g (55% yield) with HPLC purity 98%.

Example 16

A mixture of 100 g (436 mmol) of 2-((2,4-dimethylphenyl)thio)aniline (7) and bis(2-chloroethyl)amine hydrochloride (8) (85 g, 480 mmol) are charged in Chlorobenzene (4 v, 400 mL) and maintained at 130-135° C. for 25-30 h. After completion, the reaction mixture is cooled to 20° C.-35° C., and the reaction mixture is diluted with toluene (4 v) and maintain for 2 h under stirring. The solid mass is filtered and washed with 1 v of toluene to get 1-(2-((2,4-dimethylphenyl)thio)phenyl)piperazine hydrochloride (9) solid. The isolated weight 68 g (45% yield) with HPLC purity 97%.

Example 17

A mixture of 100 g (436 mmol) of 2-((2,4-dimethylphenyl)thio)aniline (7) and bis(2-chloroethyl)amine hydrochloride (8) (85 g, 480 mmol) are charged into Sulfolane (4 v, 400 mL) and maintained at 150-155° C. for 15-18 h. After completion, the reaction mixture is cooled to 40° C. and diluted with acetone (4 v) and maintain for 2 h under stirring. The solid mass is filtered and washed with 1 v of acetone to get 1-(2-((2,4-dimethylphenyl)thio)phenyl)piperazine hydrochloride (9) solid. The isolated weight is 85 g (56% yield) with HPLC purity 96%.

Example 18

A mixture of 100 g (436 mmol) of 2-((2,4-dimethylphenyl)thio)aniline (7) and bis(2-chloroethyl)amine hydrochloride (8) (85 g, 480 mmol) are charged into N-Methyl-2-Pyrrolidone (4 v, 400 mL) and maintained at 150-155° C. for 18-20 h. After completion, the reaction mixture is cooled to 40° C. and diluted with toluene (4 v) and water (4 v), later maintained at 10-15° C. for 1 h under stirring. The solid mass is filtered and washed with 1 v of toluene to get 1-(2-((2,4-dimethylphenyl)thio)phenyl)piperazine hydrochloride (9) as light brown solid. The isolated weight is 88 g (60% yield) with HPLC purity 94%.

G. Preparation of 1-(2-((2,4-dimethylphenyl)thio) phenyl)piperazine hydrobromide (11)

Method A

Example 19

1-(2-((2,4-dimethylphenyl)thio)phenyl)piperazine hydrochloride (9) 100 g (229 mmol) is charged in to 1 L flask with methanol (3 v, 300 mL) at 20° C.-35° C. Aq HBr 48% (72 g, 450 mmol) is added dropwise into reaction mixture over a period of 15 min at 30-35° C., and maintained for 3-4 h at 20° C.-35° C. The solid mass is filtered and washed with cold methanol (1 v) to get 1-(2-((2,4-dimethylphenyl)thio) phenyl)piperazine hydrobromide as white solid. The isolated weight is 85 g (75% yield) with HPLC purity 99.6%.

Example 20

1-(2-((2,4-dimethylphenyl)thio)phenyl)piperazine hydrochloride (9) 5 g (14.9 mmol) is charged in to 100 mL flask with ethanol (3 v, 15 mL) at 20° C.-35° C. Aq HBr 48% (1.8 g, 22.3 mmol) is then added dropwise into reaction mixture over a period of 10 min at 30-35° C., and maintained for 3-4 h at 20° C.-35° C. The solid mass is filtered and washed with cold ethanol (1 v) to get 1-(2-((2,4-dimethylphenyl)thio) phenyl)piperazine hydrobromide as white solid. The isolated weight is 3.9 g (70% yield) with HPLC purity 99.7%.

Example 21

1-(2-((2,4-dimethylphenyl)thio)phenyl)piperazine hydrochloride (9) (5 g, 14.9 mmol) is charged in to 100 mL flask with Isopropyl acetate (3 v, 15 mL) at 20° C.-35° C. Aq HBr 48% (1.8 g, 22.3 mmol) is added dropwise in to reaction mixture over a period of 10 min at 30-35° C., and the reaction mixture is maintained for 3-4 h at 20° C.-35° C. The solid mass is filtered and washed with Isopropyl acetate (1 v) to get 1-(2-((2,4-dimethylphenyl)thio)phenyl)piperazine hydrobromide as white solid. The isolated weight is 4.0 g (72% yield) with HPLC purity 99.6%.

Example 22

1-(2-((2,4-dimethylphenyl)thio)phenyl)piperazine hydrochloride (9) 5 g (14.9 mmol) is charged in to 100 mL flask with Butan-2-ol (3 v, 15 mL) at 20° C.-35° C. Aq HBr 48% (1.8 g, 22.3 mmol) is added dropwise in to reaction mixture over a period of 10 min at 30-35° C. for 3-4 h at 20° C.-35° C. The solid mass is filtered and washed with Butan-2-ol (1 v) to get 1-(2-((2,4-dimethylphenyl)thio)phenyl)piperazine hydrobromide as white solid. The isolated weight 4.2 g (75% yield) with HPLC purity 99.58%.

H: Preparation of 1-(2-((2,4-dimethylphenyl)thio)phenyl)piperazine hydrobromide (11)

Method-B

Example 23

A mixture of 1-(2-((2,4-dimethylphenyl)thio)phenyl)piperazine hydrochloride (9) (100 g, 229 mmol) and Aq ammonia (3 v, 300 mL) are charged in to 1 L flask with toluene (5 v, 500 mL) at 20° C.-35° C. and stirred for 30 min. The organic layer is separated and the toluene is distilled under reduced pressure to get 1-(2-((2,4-Dimethylphenyl)thio)phenyl)piperazine free base.

The solid mass is charged into methanol (3 v) layer containing fumaric acid (15.5 g, 133 mmol) and maintained for 2 h under stirring to beget 1-(2-((2,4-Dimethylphenyl)thio)phenyl)piperazine fumarate salt (10) as white solid. Again fumarate salt converted to free base by using Aq ammonia and extracted with toluene. The organic toluene-layer is separated and distilled under reduced pressure to get 1-(2-((2,4-Dimethylphenyl)thio)phenyl)piperazine free base.

The solid mass is suspended with methanol (3 v) at 20° C.-35° C. followed by dropwise addition of Aq HBr 48% (72 g, 450 mmol) in to reaction mixture over a period of 15 min at 30-35° C. The reaction mixture is maintained for 3-4 h at 20° C.-35° C. The solid mass is filtered and washed with cold methanol (1 v) to get 1-(2-((2,4-dimethylphenyl)thio)phenyl)piperazine hydrobromide as white solid. The isolated weight 85 g (75% yield) with HPLC purity 99.7%.

The present invention thus provides a unique cost effective and environmentally benign method for the preparation of 1-(2-((2,4-Dimethylphenyl)thio)phenyl)piperazine and its salts. The novel intermediate adds value to the process as the compound has good shelf life and is easily prepared leading to target compound.

We claim:

1. A method of preparation of 1-(2-((2,4-Dimethylphenyl)thio)phenyl) piperazine and its salts, said method comprising acts of— a) preparing 2-Mercaptobenzoic acid (2) from 2,2'-disulfanediyldibenzoic acid (1) in a solvent in presence of base and metal catalyst, b) coupling 2-Mercaptobenzoic acid (2) with 1-Bromo-2,4-dimethylbenzene (4) to obtain 2-((2,4-dimethylphenyl)thio)benzoic acid (5) in presence of metal catalyst, c) reacting 2-((2,4-dimethylphenyl)thio)benzoic acid (5) with halogenating agent and hydroxyl amine hydrochloride to obtain 2-((2,4-dimethylphenyl)thio)-N-hydroxybenzamide (6), d) heating 2-((2,4-dimethylphenyl)thio)-N-hydroxybenzamide (6) in presence of base to obtain 2-((2,4-dimethylphenyl)thio) aniline and converting to 2-((2,4-dimethylphenyl)thio) aniline hydrochloride (7), e) reacting 2-((2,4-dimethylphenyl)thio) aniline hydrochloride (7) with Bis(2-chloroethyl)amine hydrochloride (8) to obtain 1-(2-((2,4-Dimethylphenyl)thio)phenyl) piperazine hydrochloride (9), and f) converting 1-(2-((2,4-Dimethylphenyl)thio)phenyl) piperazine hydrochloride (9) optionally to obtain 1-(2-((2,4-Dimethylphenyl)thio)phenyl) piperazine or its salt.

2. The method as claimed in claim 1, wherein the metal catalysts are selected from zinc and copper.

3. The method as claimed in claim 1, wherein the halogenating reagent is selected from a group comprising Sodium hypochlorite, Phosphorus trichloride, Phosphorus pentachloride, and Thionyl chloride.

4. A compound of formula (6)

Formula (6)

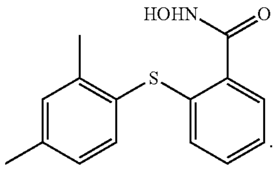

5. A method of preparation of 1-(2-((2,4-Dimethylphenyl)thio)phenyl) piperazine and its salts, said method comprising acts of a) heating 2-((2,4-dimethylphenyl)thio)-N-hydroxybenzamide (6) in presence of base in a solvent to obtain 2-((2,4-dimethylphenyl)thio) aniline and converting to 2-((2,4-dimethylphenyl)thio) aniline hydrochloride (7), b) reacting 2-((2,4-dimethylphenyl)thio) aniline hydrochloride (7) with Bis(2-chloroethyl)amine hydrochloride (8) in a solvent to obtain 1-(2-((2,4-Dimethylphenyl)thio)phenyl) piperazine hydrochloride (9), and c) converting 1-(2-((2,4-Dimethylphenyl)thio)phenyl) piperazine hydrochloride (9) optionally to 1-(2-((2,4-Dimethylphenyl)thio)phenyl) piperazine or its salts.

6. The method as claimed in claim 1, wherein the salt is 1-(2-((2,4-Dimethylphenyl)thio)phenyl) piperazine fumarate (10) or 1-(2-((2,4-Dimethylphenyl)thio)phenyl) piperazine hydrobromide (11).

7. The method as claimed in claim 1, wherein the base is selected from a group comprising Sodium hydroxide, Potassium hydroxide, Sodium methoxide, Sodium carbonate, Potassium carbonate, Sodium bicarbonate, Triethylamine, Triazabicyclodecene, 1,8-Diazabicyclo[5.4.0]undec-7-ene, and 1,5-Diazabicyclo[4.3.0]non-5-ene.

8. The method as claimed in claim 1, wherein the solvent is selected from a group comprising solvents of Toluene, Ethylene dichloride, 1,4-Dioxane, Diglyme, Monoethylene Glycol, Sulfolane, n-Butanol, Chlorobenzene, Dichlorobenzene, m-Xylene, Methanol, Isopropyl acetate, Isobutanol, Dimethyl Sulfoxide, N-Methyl-2-Pyrrolidone and Dimethylacetamide.

9. The method as claimed in claim 1, wherein the 2-((2,4-dimethylphenyl)thio)-N-hydroxybenzamide (6) is heated at a temperature ranging from 60° C. to 75° C.

10. The method as claimed in claim 6, wherein 1-(2-((2,4-Dimethylphenyl)thio)phenyl)piperazinehydrobromide salt (11) is of purity ranging from 99.6% to 99.7%.

11. The method as claimed in claim 5, wherein the salt is 1-(2-((2,4-Dimethylphenyl)thio)phenyl) piperazine fumarate (10) or 1-(2-((2,4-Dimethylphenyl)thio)phenyl) piperazine hydrobromide (11).

12. The method as claimed in claim 5, wherein the base is selected from a group comprising Sodium hydroxide, Potassium hydroxide, Sodium methoxide, Sodium carbonate, Potassium carbonate, Sodium bicarbonate, Triethylamine, Triazabicyclodecene, 1,8-Diazabicyclo[5.4.0]undec-7-ene, and 1,5-Diazabicyclo[4.3.0]non-5-ene.

13. The method as claimed in claim 5, wherein the solvent is selected from a group comprising solvents of Toluene, Ethylene dichloride, 1,4-Dioxane, Diglyme, Monoethylene Glycol, Sulfolane, n-Butanol, Chlorobenzene, Dichlorobenzene, m-Xylene, Methanol, Isopropyl acetate, Isobutanol, Dimethyl Sulfoxide, N-Methyl-2-Pyrrolidone and Dimethylacetamide.

14. The method as claimed in claim 5, wherein the 2-((2,4-dimethylphenyl)thio)-N-hydroxybenzamide (6) is heated at a temperature ranging from 60° C. to 75° C.

15. The method as claimed in claim 11, wherein 1-(2-((2,4-Dimethylphenyl)thio)phenyl)piperazinehydrobromide salt (11) is of purity ranging from 99.6% to 99.7%.

* * * * *